United States Patent [19]

Baum et al.

[11] 4,291,171

[45] Sep. 22, 1981

[54] ESTERS OF 2-FLUORO-2,2-DINITROETHYLMALONATE AND 2,2-DINITROPROPYLMALONATE

[75] Inventors: Kurt Baum, Pasadena; Allen M. Guest, San Dimas, both of Calif.

[73] Assignee: The United States of America as represented by the Secretary of the Navy, Washington, D.C.

[21] Appl. No.: 179,863

[22] Filed: Aug. 20, 1980

[51] Int. Cl.$^3$ .............................................. C07C 79/41
[52] U.S. Cl. ...................................... 560/156; 149/88
[58] Field of Search ........................................ 560/156

[56] References Cited

U.S. PATENT DOCUMENTS

| | | | |
|---|---|---|---|
| 2,999,099 | 9/1961 | Feuer | 560/156 |
| 3,359,334 | 12/1967 | Gold | 560/156 |
| 3,624,129 | 11/1971 | Kamley | 560/156 |
| 3,732,289 | 5/1973 | Gold | 560/156 |
| 3,872,159 | 3/1975 | Marcus | 560/156 |

*Primary Examiner*—Natalie Trousof
*Assistant Examiner*—Michael Shippen
*Attorney, Agent, or Firm*—R. S. Sciascia; A. L. Branning; R. D. Johnson

[57] ABSTRACT

Dimethyl 2,2,2-trinitroethylmalonate, diethyl 2,2,2-trinitroethylmalonate, dimethyl 2-fluoro-2,2-dinitroethylmalonate, diethyl 2-fluoro-2,2-dinitroethylmalonate, dimethyl 2,2-dinitropropylmalonate, diethyl 2,2-dinitropropylmalonate, and methods of preparing these compounds. These compounds are useful as energetic additives to propellants and explosives.

4 Claims, No Drawings

ESTERS OF 2-FLUORO-2,2-DINITROETHYLMALONATE AND 2,2-DINITROPROPYLMALONATE

BACKGROUND OF THE INVENTION

This invention relates to organic esters and more particularly nitro-substituted malonates.

The reaction of diethyl methylenemalonate with diethyl malonate catalyzed by piperidine or potassium hydroxide has been reported in the literature. In the area of nitroalkane chemistry, the Michael reaction with α,β-unsaturated carbonyl compounds is one of the most useful methods of introducing functionality. However, nitro- and fluoronitro-substituted malonates have not been prepared in the prior art. Because of the reactivity of the malonates, these compounds would be valuable intermediates in the synthesis of other nitro- and fluoronitro-substituted compounds and polymers for use in propellants and explosives.

SUMMARY OF THE INVENTION

Accordingly, one object of this invention is to provide new organic compounds.

Another object of this invention is to provide new energetic explosive organic compounds.

A further object of this invention is to provide reactive organic compounds which may be used to add nitro and fluoronitro groups to unsaturated polymers and other organic compounds used in explosives and propellants.

These and other objectives of this invention are achieved by providing a compound of the formula

$$R-CH(CO_2R')_2$$

wherein R is selected from the group consisting of $C(NO_2)_3CH_2-$ $CF(NO_2)_2CH_2-$ and $CH_3C(NO_2)_2CH_2-$, and wherein R' is selected from the group consisting of $CH_3-$ and $CH_3CH_2-$. These compounds are useful as energetic additives to propellants and explosives.

DETAILED DESCRIPTION OF THE PREFERRED EMBODIMENT

Highly reactive nitro-substituted dimethyl and diethyl malonates are prepared by reacting dimethyl or diethyl methylenemalonate with nitroform, 1,1-dinitroethane, or fluorodinitromethane. The desired products include dimethyl 2,2,2-trinitroethylmalonate, diethyl 2,2,2-trinitroethylmalonate, dimethyl 2,2-dinitropropylmalonate, diethyl 2,2-dinitropropylmalonate, dimethyl 2-fluoro-2,2-dinitroethylmalonate, and diethyl 2-fluoro-2,2-dinitroethylmalonate.

Carefully controlled reaction conditions are required because the addition of a nucleophile (nitro- or halonitroalkyl ion) to a methylenemalonate ester gives the salt of an alkylmalonate which is itself capable of undergoing further nucleophilic reactions. Nitroform, a strong acid, reacts with diethyl methylenemalonate in aqueous methanol at ambient temperature, without a base as catalyst, to produce diethyl 2,2,2-trinitroethylmalonate. The same conditions may also be used to produce dimethyl 2,2,2-trinitroethylmalonate. The reaction of 1,1-dinitroethane with methylenemalonates does not take place under these conditions, presumably because the nitro compound is not sufficiently ionized. However, the addition of triethylamine to an ether solution of 1,1-dinitroethane and dimethyl methlenemalonate at 0° C. resulted in a 72% yield of dimethyl 2,2-dinitropropylmalonate. In the same manner, diethyl 2,2-dinitropropylmalonate may be prepared. Finally, the addition fluorodinitromethane to methylenemalonates in ether solution in the presence of catalytic amounts of pyridine produces good yields of dimethyl and diethyl 2-fluoro-2,2-dinitroethylmalonates.

The general nature of the invention having been set forth, the following examples are presented as specific illustrations thereof. It will be understood that the invention is not limited to these specific examples but is susceptible to various modifications that will be recognized by one of ordinary skill in the art.

Nuclear magnetic resonance and infrared spectra were recorded with a Varian T-60 spectrometer and a Perkin-Elmer 700 spectrometer, respectively.

Diethylene methylene malonate was synthesized by a method disclosed by G. B. Bauchman and H. A. Tanner in "Diethyl Methylenemalonate," *J. Org. Chem.*, 4, 493 (1939). The following procedure is quoted from that article:

"Diethyl methylene malonate. To 200 g of glacial acetic acid were added 30 g of paraformaldehyde, 80 g of malonic ester, 5 g of copper acetate and 5 g of potassium acetate. The mixture was heated on the steam bath until clear (about an hour) and for an hour longer. It was then distilled under diminished pressure until the b.p. reached 130° at 35 mm. At this point the contents of the distilling flask began to thicken to a paste. The receiver was changed, and the distillation continued. The blue-colored paste seemed to foam up and decompose, the product being evolved during the decomposition. When the distillation temperature reached 200° and the paste had turned dark-brown distillation was stopped. The greenish-yellow distillate solidified on standing to the waxy polymer. It was, however, impure. Redistillation yielded a fraction boiling at 205°–215° which was nearly pure diethylmethylene malonate and suitable for the preparation of co-polymers or diene adducts. Yield 36.8 g or 46% theoretical (based on malonic ester). By repeated fractionation, or by distillation through a column under diminshed pressure a very pure product was obtained, although the losses at each step were considerable. The purest sample showed the following constants: b.p. 210° at 760 mm.; $n_D^{23}$ 1.432; $d_4^{23}$ 1.052.

Anal. Calc'd. for $C_8H_{12}O_4$: C, 55.82; H, 6.98. Found: C, 55.88; H, 7.01."

Dimethyl methylene malonate is prepared in the same way.

The fluorodinitromethane was synthesis by a process disclosed by Kurt Baum, "Direct Fluoronation of Secondary Nitronate Salts," *J. Org. Chem.*, 35, 846 (1970). The following procedure is quoted from that article:

"Fluorodinitromethane. A solution of 100 g (0.65 mol) of 2-fluoro-2,2-dinitroethanol in 280 ml of concentrated sulfuric acid and 165 ml of water was added with stirring, over a 30-min period, to a solution of 400 g (1.34 mol) of sodium dichromate dihydrate in 800 ml of water at 25°–40°. The solution was allowed to stand at ambient temperature for 66 hr and then extracted with three 300-ml portions of methylene chloride. Distillation through a 25-cm Holzmann column gave 38 g (47% conversion, 63% yield) of fluorodinitromethane, bp 40° (20 mm), and 19.0 g of 2-fluoro-2,2-dinitroethanol, bp 38°–39° (0.1 mm). An additional 6.2 g of 2-fluoro-2,2-dinitroethanol was recovered by diluting the aqueous layer with an equal volume of water and extracting with ether.

U.S. Pat. No. 3,435,079, entitled "Fluorodinitromethane and Preparation of Halodinitromethanes," which issued to Horst G. Adolph and Mortimer J. Kamlet on Mar. 25, 1969, discloses the synthesis of fluorodinitromethane from 1-fluoro-1,1-dinitroethanol, herein incorporated by reference.

The preparation of fluorodinitromethane by the reaction of an alkali metal salt of dinitromethane and fluorine is disclosed in U.S. Pat. No. 3,274,264, entitled "Fluorodinitroalkane Preparation", which issued on Sept. 20, 1966, herein incorporated by reference.

Nitroform and 1,1-dinitroethane are commercially available.

Caution: Polynitro compounds are potentially sensitive explosives, and safety precautions should be exercised.

EXAMPLE 1

Diethyl 2,2,2-Trinitroethylmalonate

Freshly distilled diethyl methylene-malonate (8.0 g, 0.046 mol) was added dropwise with stirring over a 10 min period to a solution of 16 g (0.1 mol) of nitroform in 25 ml of water and 40 ml of methanol at 0°–5°. The mixture was stirred 16 hrs at room temperature and was then extracted with 100 ml of methylene chloride. The methylene chloride solution was washed with 10% sodium bicarbonate and with water, dried over sodium sulfate and stripped of solvent under vacuum. Column chromatography on 200 g of silica gel ($CCl_4$—$CH_2Cl_2$), filtration through charcoal and removal of solvent gave 13.0 g (87%) of diethyl 2,2,2-trinitroethylmalonate, mp 24°–25°; NMR ($CDCl_3$), 4.23 (q, 4 H, J=7 Hz, C$\underline{H}_2$CH$_3$), 3.80 (m, 3 H, C$\underline{H}$—C$\underline{H}_2$) and 1.33 (t, 6 H, J=7 Hz, CH$_3$); IR (neat) 1730 (C=O) and 1600 (NO$_2$) cm$^{-1}$.

Anal. Calcd for $C_9H_{13}N_3O_{10}$: C, 33.44; H, 4.05; N, 13.00. Found: C, 33.36; H, 3.80; N, 12.92

EXAMPLE 2

Dimethyl 2,2-Dinitropropylmalonate

Triethylamine was added dropwise to a solution of 1.4 g (0.010 mol) of dimethyl methylenemalonate and 1.6 g (0.0133 mol) of 1,1-dinitroethane in 15 ml of ether at 0°, until yellow coloration persisted in the solution. The solution was allowed to stand 1 hr at ambient temperature and was then washed with 10% sodium bicarbonate, 1 N hydrochloric acid and water. The solution was dried over sodium sulfate, and the solvent was removed under vacuum. Column chromatography on a 100 g column of silica gel ($CCl_4$—$CH_2Cl_2$) and recrystallization of the product (methylene chloride-hexane, −78°) gave 1.9 g (72%) of dimethyl 2,2-dinitropropylmalonate, a white crystalline solid, mp 44°: NMR ($CDCl_3$) 3.75 (s, 6 H, CH$_3$), 3.1–3.5 (m, 3 H, C$\underline{H}$C$\underline{H}_2$) and 2.13 (s, 3 H, C—CH$_3$); IR (neat) 1730 (C=O) and 1570 cm$^{-1}$ (NO$_2$).

Anal. Calcd for $C_8H_{12}N_2O_8$: C, 36.37; H, 4.58; N, 10.60. Found C, 36.66; H, 4.61; N, 10.52.

EXAMPLE 3

Diethyl 2-Fluoro-2,2-dinitroethylmalonate

Pyridine (0.1 ml) was added over a 5 min period to a solution of 8.0 g (0.047 mol) of diethyl methylenemalonate and 7.0 (0.056 mol) of fluorodinitromethane in 60 ml of ether at −8° and the mixture was stirred at ambient temperature for 30 min. The solution was washed with 10% sodium bicarbonate and with water, dried over sodium sulfate, and stripped of solvent under vacuum. Column chromatography on 200 g of silica gel ($CCl_4$—$CH_2Cl_2$) gave 11.4 g (82%) of diethyl 2-fluoro-2,2-dinitroethylmalonate, a pale yellow oil: proton NMR ($CDCl_3$), 4.20 (q, 4 H, J=7 Hz, C$\underline{H}_2$CH$_3$), 3.2–3.6 (m, 3 H, CH$_2$CH), and 1.30 (triplet, 6 H, J=7 Hz, CH$_3$); fluorine NMR ($CDCl_3$) 103.72 (br s); IR (neat) 1730 (C=O) and 1600 cm$^{-1}$ (NO$_2$).

Anal. Calcd for $C_9H_{13}FN_2O_8$: C, 36.49; H, 4.42; N, 9.46. Found C, 36.76; H, 4.29; N, 9.70.

EXAMPLE 4

Dimethyl 2-Fluoro-2,2-dinitroethylmalonate

The above procedure using dimethyl methylenemalonate gave a 63% yield of dimethyl 2-fluoro-2,2-dinitroethylmalonate, a pale yellow oil: NMR ($CDCl_3$) 3.75 (s, 6 H, CH$_3$) and 3.2–3.6 (m, 3 H, C$\underline{H}$C$\underline{H}_2$); IR (neat) 1730 (C=O) and 1600 cm$^{-1}$ (NO$_2$).

Anal. Calcd for $C_7H_9FN_2O_8$: C, 31.35; H, 3.38; N, 10.45. Found C, 31.70; H, 3.37; N, 11.04.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. The compound, dimethyl 2-fluoro-2,2-dinitroethylmalonate.

2. The compound, diethyl 2-fluoro-2,2-dinitroethylmalonate.

3. The compound, dimethyl 2,2-dinitropropylmalonate.

4. The compounds, diethyl 2,2-dinitropropylmalonate.

* * * * *